US00PP15004P2

(12) United States Plant Patent
Redman

(10) Patent No.: US PP15,004 P2
(45) Date of Patent: Jul. 13, 2004

(54) CHRYSANTHEMUM PLANT NAMED 'MEGA TIME ROSE'

(50) Latin Name: *Chrysanthemum morifolium*
Varietal Denomination: Mega Time Rose

(75) Inventor: Ruth Redman, Bognor Regis (GB)

(73) Assignee: Cleangro LTD (GB)

( * ) Notice: Subject to any disclaimer, the term of this patent is extended or adjusted under 35 U.S.C. 154(b) by 0 days.

(21) Appl. No.: 10/364,268

(22) Filed: Feb. 10, 2003

(51) Int. Cl.[7] ..... A01H 5/00
(52) U.S. Cl. ..... Plt./297
(58) Field of Search ..... Plt./297

(56) References Cited

PUBLICATIONS

2000 Ficor catalog, listing Chrysanthemum variety 'Mega Time.' See, e.g., p. 4.
2001 Ficor catalog, listing Chrysanthemum variety 'Mega Time.' See, e.g., p. 4.
2002 Ficor catalog, listing Chrysanthemum variety 'Mega Time.' See, e.g., p. 4.

*Primary Examiner*—Anne Marie Grunberg
(74) *Attorney, Agent, or Firm*—Howrey Simon Arnold & White, LLP

(57) ABSTRACT

A new variety of Chrysanthemum plant named 'Mega Time Rose,' having a good uniform canopy of pink single flowers and a light green disc. The new variety has a medium tall vigor, free branching, uniform spreading habit and good foliage presentation.

1 Drawing Sheet

Latin name of the genus and species: Botanical classification: *Chrysanthemum morifolium.*

Variety denomination: The new Chrysanthemum variety denomination is 'Mega Time Rose.'

BACKGROUND OF THE INVENTION

The present invention comprises a new and distinct cultivar of Chrysanthemum botanically known as *Chrysanthemum morifolium*, and referred to by the cultivar name 'Mega Time Rose.'

'Mega Time Rose,' identified as 20929-12, originated from a whole plant mutation grown in a controlled planting of the unpatented variety in 'Mega Time' in Vinnetrow Road, Chichester, West Sussex, United Kingdom. The new variety 'Mega Time Rose' has been asexually reproduced by vegetative cuttings in Chichester, West Sussex, United Kingdom, and the distinguishing characteristics are retained through successive generations of asexual reproduction.

BRIEF SUMMARY OF THE INVENTION

'Mega Time Rose' is a pot type of Chrysanthemum plant variety having pink single flowers and a light green disc.

Comparison with Parent

Plants of the new Chrysanthemum variety 'Mega Time Rose' are similar to the parent cultivar 'Mega Time' in plant habitat and growth rate. In side-by-side comparisons in Chichester, West Sussex, United Kingdom, under commercial practice, plants of the new Chrysanthemum variety 'Mega Time Rose' compared to the plants of the parent cultivar 'Mega Time' in the following characteristics.

1. The new variety 'Mega Time Rose' produces pink flowers whereas the parent cultivar 'Mega Time' produces light pink flowers.
2. Plants of the new variety 'Mega Time Rose' have similar inflorescence to the plants of the parent cultivar 'Mega Time.'

Comparison with Other Varieties

Plants of the new Chrysanthemum variety 'Mega Time Rose' are similar to the unpatented cultivar 'Irvine' in plant habit and growth rate. However in side-by-side comparisons in Chichester, West Sussex, United Kingdom, under commercial practice, plants of the new Chrysanthemum variety 'Mega Time Rose' differed from plants of the cultivar 'Irvine' in the following characteristics.

1. The new variety 'Mega Time Rose' produces pink single flowers whereas the cultivar 'Irvine' produces dark pink flowers.
2. Plants of the new variety 'Mega Time Rose' have larger and taller inflorescence than plants of the cultivar 'Irvine'.

BRIEF DESCRIPTION OF ILLUSTRATION

Typical specimens of the plant and flowers for the new Chrysanthemum variety 'Mega Time Rose' are shown in the accompanying digital photograph. The colors shown are as true as possible within the usual limits of this kind of illustration.

FIG. 1 is a whole plant view of the new variety 'Mega Time Rose' grown in a pot. The plant shown in the illustration is 54 days from the commencement of Short Days.

DETAILED BOTANICAL DESCRIPTION

The following description of the new Chrysanthemum variety 'Mega Time Rose' is of plants grown in a greenhouse in Chichester, West Sussex, United Kingdom in the month of May. The cultivar has not been observed under all possible environmental conditions. The phenotype may vary significantly with variations in the environment such as temperature, length of day and light intensity, without any variance in genotype. The commercial classification of the new variety is a pot Chrysanthemum.

Plants of the new variety have been grown successfully under temperature conditions averaging about 19° C. at night and about 17° C. to 24° C. during the day under light conditions of about 5000 to 6000 foot candles. The plants respond well to the use of growth retardant, such as B9 treatment at about 2 g per liter. To produce a commercial product the plants may be pinched once with the center bud removed. The typical container size for commercial growth is 1 liter. It has been observed that the shelf life of the new variety is about 21 days with a response time of about 7.5 weeks. The new variety is suitable for growth in a temperature range of 15° C. to 25° C.

The new variety may be produced as a spray. The following description is with respect to a plant produced as a pot Chrysanthemum. In the description of this new Chrysanthemum variety, color values have been taken from The Royal Horticultural Society Colour Chart (R.H.S.C.C.).

Plant

Plant type: Pot.
Habit: Upright end free branching.
Height: 24 cm.
Width: 35 cm.
Branching characteristics: Upright and free branching.
Length of lateral branches: 19 cm.
Number of breaks from pinch: 5.
Stem color: 137B.
Response time: 51 days.
Vigor: Medium/Tall.
Shelf life: 21 days.
Disease/pest (susceptibility/resistance observed): None observed to date.
Growth retardant type and treatment: 3 applications of 2.5 gm/liter B9 @ 2, 21 and 28 days after sticking unrooted cuttings.

The plants were grown for 2 weeks in Long Day conditions (20 hours of light) and then transferred to Short Day conditions (13 hours of dark).

Propagation:
*Type.*—Vegetative propagation via stem cuttings.
*Time to rooting.*—14 days with soil temperatures of 18° C.
*Rooting habit.*—After 7 Long Days the first roots emerge and form root primordia. In 14 Long Days a complete root system is developed.

Foliage

Number of leaves per lateral branch: 12.
Compound or single: Single.
Arrangement of leaves: Alternate.
*Shape of leaf.*—Typically 5 lobed ovate.
*Size of leaf.*—Width (cm): 4 Length (cm): 6.
*Leaf apex.*—Acute.
*Base.*—Obtuse.
*Attachment.*—petioled.
*Aspect.*—Slight undulating.
*Margin.*—Palmately lobed.
*Surface characteristics.*—Top: slightly pubescent. Bottom: pubescent.
Petiole: Color: 137D. Length: 1.5 cm.
Venation: Net, prominent mid vein at underside. Color: Upper side: near 137C. Under side: near 138B.
Color: Mature Leaf, upper side: near 137B; under side: near 138A. Young Leaf, upper side: near 137A ; under side: near 137D.

Flower

Flower appearance: Matte.
Flower type: Single.
Flower form: Slightly cupped.
Flower shape: Round.
Flowering habit: Cyme.
Number of blossoms per branch: 6.
Inflorescence form: Cyme.
*Depth of fully expanded blossoms.*—2 cm.
*Diameter of fully expanded blossoms.*—7 cm.
Phyllaries:
*Number.*—20.
*Color.*—Near 137C.
*Length.*—0.7 to 1.2 cm.
*Width.*—0.1 to 0.3 cm.
*Texture/appearance.*—Pubescent.
Peduncle: Peduncle length is shortest at the terminal flower and progressively longer moving down the stem.
*Length.*—12 cm.
*Color.*—Near 137C.
*Surface.*—Pubescent.
*Habit.*—Slightly undulating.
*Strength.*—Medium.
Pedicel: Length: terminal: 3 cm; lateral: 4.5 cm.
*Color.*—Near 137C.
*Surface.*—Pubescent.
*Habit.*—Slightly undulating.
*Strength.*—Medium.
Ray florets:
*Form/shape.*—Straight and spatulate.
*Texture/appearance.*—Shiny.
*Number per flower.*—25.
*Length.*—3.5 cm; Width: 1 cm.
*Apex.*—Rounded.
*Base.*—Tapered.
*Margin.*—Entire.
Disc florets:
*Form/shape.*—Cylindric.
*Texture/appearance.*—Shiny.
*Number per flower.*—120.
*Length.*—0.6 cm; Width: 0.1 cm.
*Diameter of disc.*—1.3 cm.
Fragrance: None.
Flower bud (at onset of color):
*Length.*—1 cm.
*Diameter.*—1 cm.
*Form/shape.*—Spherical.
General flower color:
1. *Ray florets, upper side.*—78B. Immature: near 78A. Mature: near 78B. Older/Fading: near 77C.
2. *Ray florets, under side.*—78C. Immature: near 78B. Mature: near 78C. Older/Fading: near 77D.
3. *Disc florets.*—Immature: near 152C. Mature: near 15C. Older/Fading: near 15C.
4. *Bud.*—78C.

Flower progression with age: Flower form does not change but there is little color changes with age.

Reproductive Organs

Gynoecium present on Ray and Disc florets.

Ray florets:
*Pistil number.*—25.
*Stigma color.*—Near 154A.
*Stigma shape.*—Forked.

*Style color.*—Near 154B.
*Style length.*—0.3 cm.
Disc florets:
*Pistil number.*—120.
*Stigma color.*—Near 154A.
*Stigma shape.*—Forked.
*Style color.*—Near 154A.
*Style length.*—0.3 cm.

Androecium: Not observed.
Fruit and seeds: None observed.

What is claimed is:

1. A new and distinct variety of Chrysanthemum plant, substantially as described and illustrated herein.

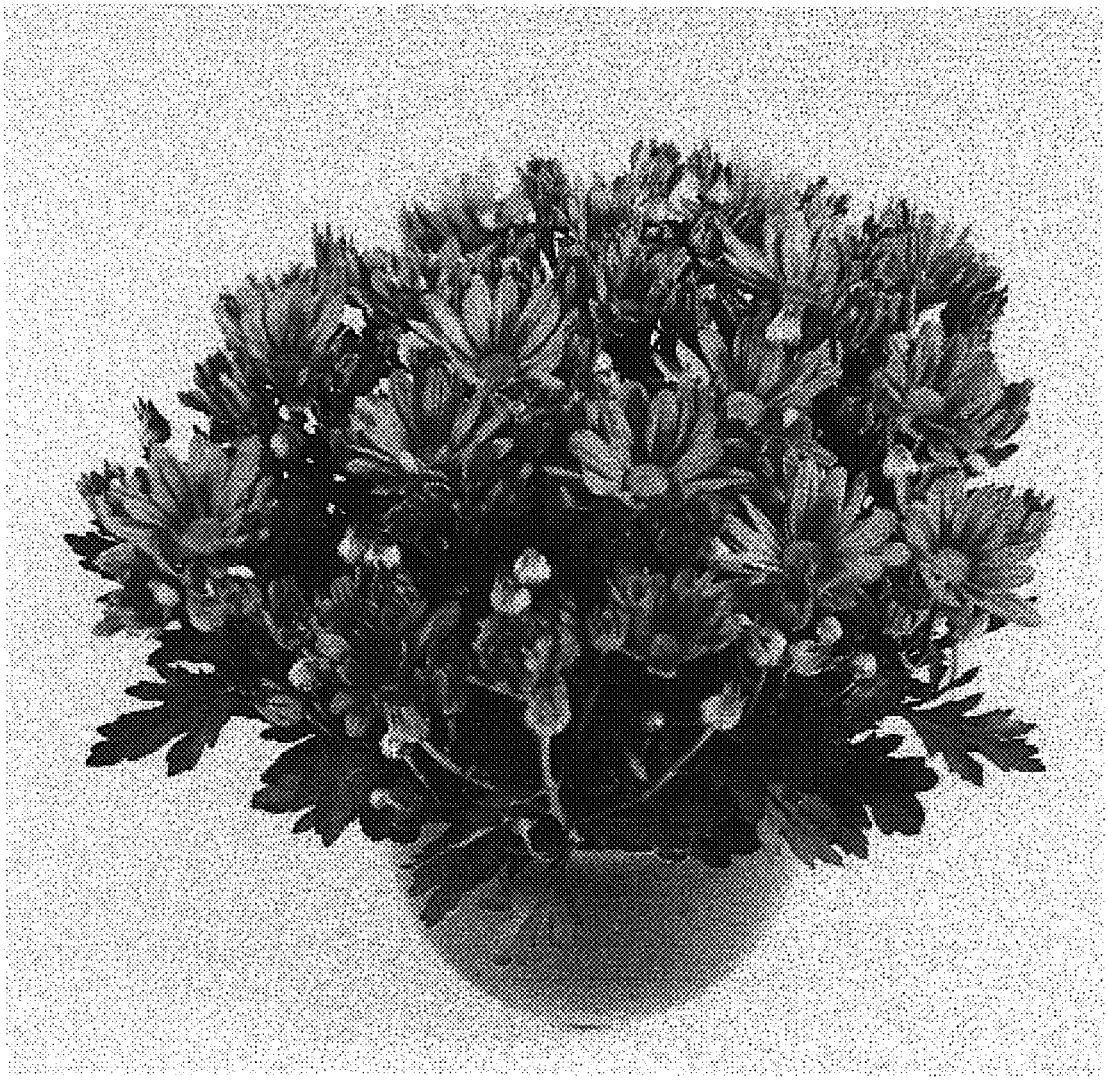

* * * * *